United States Patent [19]
Fagher et al.

[11] Patent Number: 5,834,497
[45] Date of Patent: Nov. 10, 1998

[54] USE OF FELODIPINE TO TREAT CEREBRAL DYSFUNCTION DUE TO SOLVENT EXPOSURE

[75] Inventors: Birger Fagher, Lund; Lars Jönsson, Mölndal; May Lindgren, Oskarshamn; Stephen Partridge, Mölndal; Dag Elmfeldt, Hovås, all of Sweden

[73] Assignee: Astra Aktiebolag, Sodertalje, Sweden

[21] Appl. No.: 648,000

[22] PCT Filed: May 8, 1996

[86] PCT No.: PCT/SE96/00601

§ 371 Date: May 30, 1996

§ 102(e) Date: May 30, 1996

[87] PCT Pub. No.: WO96/36337

PCT Pub. Date: Nov. 21, 1996

[30] Foreign Application Priority Data

May 15, 1995 [SE] Sweden .................................. 9501773

[51] Int. Cl.$^6$ ....................................................... A61K 31/44
[52] U.S. Cl. .............................................................. 514/356
[58] Field of Search ............................................... 514/356

[56] References Cited

FOREIGN PATENT DOCUMENTS 9310781  6/1993  WIPO .

OTHER PUBLICATIONS

G. Zupan, et al., Arch. Int. Pharmacodyn, vol. 325, pp. 61–69, (1993) Effects of Nicardipine, Felodipine and Nifedipine on Passive Avoidance Behavior of Intact and Hypoxia–Exposed Rats.

Primary Examiner—William R. A. Jarvis
Attorney, Agent, or Firm—White & Case L.L.P.

[57] ABSTRACT

This invention relates to the use of felodipine or a pharmaceutically acceptable salt thereof for the treatment of cerebral dysfunction due to solvent exposure.

2 Claims, No Drawings

USE OF FELODIPINE TO TREAT CEREBRAL DYSFUNCTION DUE TO SOLVENT EXPOSURE

This application is a 371 PCT/SE96/00601, filed May 8, 1996.

FIELD OF THE INVENTION

The present invention is related to the use of 2,6-dimethyl-4-(2,3-dichlorophenyl-1,4-dihydropyridine-3,5-dicarboxylic acid-3-methyl-5-ethyl ester, generic name felodipine, in the form of the racemate or an optical isomer as well as pharmaceutically acceptable salts thereof, for the treatment of cerebral dysfunction due to solvent exposure and in the manufacture of pharmaceutical preparations with effect on cerebral dysfunction due to solvent exposure.

BACKGROUND OF THE INVENTION

Felodipine, which is described in the European patent EP 7293, is a dihydropyridine calcium antagonist which has been shown in hypertensive patients to lower blood pressure through a direct effect on the resistance vessels (small arteries). However, no effect on cerebral dysfunction due to solvent exposure has been reported earlier.

By dysfunction due to solvent exposure is in this context meant altered cognative functioning, in particular impaired memory ability, psychomotor capacity and reaction times.

PRIOR ART

No specific treatment of cerebral dysfunction due to solvent exposure is available today.

OUTLINE OF THE INVENTION

It has now been found that felodipine is effective in the treatment of cerebral dysfunction due to solvent exposure, which produces a dementia like disease. Various solvents may produce a dementia like disease. Examples of such solvents are organic solvents both chlorinated and non-chlorinated. Improvement of cerebral dysfunction can also be expected when caused by agents other than a solvent The compound 2,6-dimethyl-4-(2,3-dichlorophenyl1,4-dihydropyridine-3,5-dicarboxylic acid-3-methyl-5-ethyl ester and pharmaceutically acceptable salts thereof, can be prepared by processes known in the art, see e.g. EP 7293.

Felodipine may be in the form of its optical antipodes or the racemate; the effect of this compound on cerebral dysfunction due to solvent exposure and dementia is obtained with the racemic mixture as well as the separate isomeric forms.

Pharmaceutically acceptable salts of felodipine can be prepared from inorganic and organic acids including for example acetic, benzene-sulfonic, benzoic, camphorsulfonic, citric, ethenesulfonic, fumaric, gluconic, glutamic, hydrobromic, hydrochloric, isethonic, lactic, maleic, malic, mandelic, methanesulfonic, mucic, nitric, pamoic, pantothenic, phosphoric, succinic, sulfuric, tartaric, and p-toluenesulfonic acids.

Conventional pharmaceutical preparations can be used.

The pharmaceutical preparations are preferably in the form of tablets or capsules, but it is also possible to use other kinds of preparations, such as oral solutions or suspensions or injection solutions. Extended release formulations can also be used.

Unit dose pharmaceutical preparations usually contain 5 to 20 mg of felodipine, preferably 10 to 15 mg. By using an oral liquid formulation it is possible to administer 1 mg/ml.

The daily dosage of felodipine for use in cerebral dysfunction due to solvent exposure and dementia is 5 to 20 mg per day.

EXPERIMENTAL DATA

Three male patients with solvent induced chronic toxic encephalopathy were treated with felodipine during a period of 3 to 5 months.

The patients were examined with semi-structured interviews, Target Complaints, neuropsychological tests and cerebral blood flow examinations (Cortexplorer and SPECT) on 2 or 3 occasions. The baseline examinations were conducted twelve weeks before and again immediately before the felodipine treatment revealed servere symptoms such as sleep disturbance and headache, impaired performance in the neuropsychological testing and pathological cerebral blood flow.

At the examination after the treatment the patients' symptoms were considerably reduced. The neuropsychological testing revealed improved (at least 10 per cent) functioning in tests assessing visuo-spatial memory ability.

An increase of at least 10 per cent in the cerebral blood flow was also found in both the Cortexplorer and the SPECT examinations.

CONCLUSIONS

The case reports from 3 patients show a positive improvement in patients with chronic toxic encephalopathy, due to solvent exposure. This is a dementia like disease.

The clinical improvement is accompanied by improvements in regional cerebral blood flow.

Regional improvement in cerebral blood flow is seen in different types of dementia. Therefore, it is reasonable to conclude that felodipine exerts a beneficial effect in dementia as a result of the improvement of cerebral blood flow.

We claim:

1. A method of treating cerebral dysfunction due to solvent exposure in a patient in need thereof comprising administering to said patient a therapeutically effective amount of felodipine in the form of the racemate, an optical isomer, or a pharmaceutically acceptable salt thereof.

2. A method according to claim 1 wherein felodipine is administered in a dosage of 5 to 20 mg per day.

* * * * *